United States Patent [19]

Bizhanov et al.

[11] 4,018,835

[45] Apr. 19, 1977

[54] METHOD OF PRODUCING POLYHYDRIC ALCOHOLS

[76] Inventors: Frunze Bizhanovich Bizhanov, ulitsa Dzhambula, 180, kv. 1; Dmitry Vladimirovich Sokolsky, prospekt Abaya, 31, kv. 38; Ashim Kuranbaevich Omarov, ulitsa Dzhambula, 13, kv. 37, all of Alma-Ata; Akhmed Miftakhovich Khisametdinov, prospekt Kommunistichesky, 95, Chimkent; Sagynbek Ongarbaev, prospekt Kosmonavtov, proezd Festivalny, 7, Chimkent; Nikolai Ivanovich Popov, prospekt Kosmonavtov, 19, kv. 3, Chimkent, all of U.S.S.R.

[22] Filed: Feb. 13, 1976

[21] Appl. No.: 658,049

Related U.S. Application Data

[63] Continuation of Ser. No. 141,426, May 7, 1971, abandoned.

[52] U.S. Cl. .................. 260/635 C; 252/477 Q

[51] Int. Cl.$^2$ ............................... C07C 29/00
[58] Field of Search ............ 260/635 C; 252/477 Q

[56] References Cited

UNITED STATES PATENTS

| 2,983,734 | 5/1961 | Sargent ..................... 260/635 C |
| 3,586,537 | 6/1971 | Steiner et al. ............... 260/635 C |
| 3,615,215 | 10/1971 | VanDohren et al. ......... 252/477 Q |

FOREIGN PATENTS OR APPLICATIONS

| 216,189 | 1/1957 | Australia ..................... 260/635 C |
| 1,173,838 | 12/1969 | United Kingdom ........... 252/477 Q |

*Primary Examiner*—Joseph E. Evans

[57] ABSTRACT

A method of producing polyhydric alcohols by hydrogenation of monoses, characterized in that the hydrogenation is carried out on a skeleton nickel catalyst promoted by Fe taken in an amount of from 25 to 400 wt.% with respect to that of nickel used.

11 Claims, No Drawings

METHOD OF PRODUCING POLYHYDRIC ALCOHOLS

This application is a continuation application of Ser. No. 141,426, now abandoned, filed May 7, 1971.

The present invention relates to an improvement in the production process of polyhydric alcohols by hydrogenation of corresponding monoses.

The products of the reaction, viz., hexitols and xylitols find widespread application in food and pharmaceutical industries, as well as in the capacity of selective solvents in certain branches of chemical industry.

The conventional method of producing polyhydric alcohols is carried into effect in intermittent- and continuous-action apparatus and consists in hydrogenation of corresponding monoses in the presence of pure nickel catalysts or of those promoted by chromium or titanium additives, at a temperature of 100°–130° C and a pressure of $H_2$ equal to 100–200 atm.

Disadvantages involved in the commonly used method of producing polyhydric alcohols are as follows: use of catalysts having but relatively low activity and stability and containing such critical components as titanium, chromium and nickel.

It is an essential object of the present invention to find out a more effective catalyst to effect monose hydrogenation which would feature higher activity and stability as compared to those used currently.

Said object has been accomplished by the provision of a catalytic method of producing polyhydric alcohols which, according to the present invention resides in hydrogenation of monoses on a skeleton Ni-Fe catalyst containing from 25 to 400 wt.% Fe with respect to Ni, occurring at 20°–120° C and hydrogen pressure equal to 10–80 kg/cm².

The method disclosed herein features the following advantages: hydrogenation rate of monoses twice as high as compared to the common methods, this being due to the use a skeleton Ni-Fe catalyst; reduced nickel consumption; dispensing with the use of titanium or chromium; higher stability and activity of catalyst.

The present invention will be illustrated hereinbelow by way of examples of a specific and preferred embodiment of the method thereof.

EXAMPLE 1

A reaction vessel of a 0.55-liter capacity equipped with a 2800-rpm stirrer is charged with 400 ml of a 16-percent aqueous glucose solution and a catalyst resulting from leaching of an alloy of Ni:Al:Fe=25:50:25 at 100° C for one hour (taken at a rate of 2 g per 160 ml of a 20-percent aqueous caustic) and carefully washed from traces of the leach liquor. Then air is expelled from the reaction vessel by the stream of $H_2$, the vessel is hermetically sealed and a required pressure is established in the system. This done, the stirrer drive motor and the heater are switched on, the latter ensuring temperature rise and keeping it in the course of hydrogenation. A valve and pressure gauge are provided to control and maintain a constant pressure of $H_2$ in the system during the reaction. The extent of conversion of monoses is judged by analyzing samples taken every 0.5–1 hour throughout the process of hydrogenation.

Hydrogenation conditions are as follows: temperature of 110° C; hydrogen pressure of 50 kg/cm²; amount of the alloy of Ni:Fe:Al=25:25:50 2.0 g; glucose conversion percentage: in 2 hrs - 55; in 4 hrs - 89; and in 5 hrs - 100.

Table 1 presents comparative test data of conventional skeleton nickel catalysts and the herein-proposed Ni-Fe-Al catalysts, the test conditions being equal and as follows: temperature of 110° C; $P_{H_2}=50$ kg/cm²; amount of the respective catalyst alloy under test, 2.0 g; amount of a 16-percent glucose solution, 400 ml.

Table 1

| Nos. | Composition of catalyst, per cent | Glucose conversion percentage as against duration of hydrogenation process in hours | | | | |
|---|---|---|---|---|---|---|
| | | 1 | 2 | 3 | 4 | 5 |
| 1. | Ni:Al=50:50 | 49 | 59 | 69 | 76 | 82 |
| 2. | Ni:Al:Ti=49:50:2 | 39 | 49 | 59 | 70 | 80 |
| 3. | Ni:Al:Fe 48:50:2 | 39 | 57 | 78 | 96 | 100 |
| 4. | 45 : 50 : 5 | 45 | 63 | 80 | 98 | 100 |
| 5. | 40 : 50 : 10 | 49 | 69 | 90 | 100 | — |
| 6. | 25 : 50 : 25 | 37 | 55 | 74 | 89 | 100 |
| 7. | 10 : 50 : 40 | 29 | 39 | 50 | 60 | 69 |

As is evident from the above-tabulated data, a Fe-additive to the skeleton nickel results in higher catalyst activity. The highest activity is found in catalyst No.5 which contains 25 percent Fe with respect to Ni, i.e. has the following percentage composition: Ni, 40; Al, 50; Fe, 10. A fairly high optimum activity is featured by a catalyst, wherein the ratio of Ni and Fe is 1:1 (that indicated at No.6 in Table 1). Similar results are shown wherein the ratio of Ni and Fe is 24.1 (No. 3 in Table 1). Thus the range of Ni:Fe which gives the best results is 1:1 to 24:1. However the catalyst of No. 6 is more profitable in the process as allowing such a critically-short component as nickel to be replaced to a considerably extent by a much more easily available material, viz., Fe, its higher activity as compared to a skeleton Ni-Fe commercial catalyst remaining unaffected. The catalyst activity has been classified and compared as against the extent of conversion of glucose per equal spaces of time. High activity exhibited by skeleton Ni-Fe catalysts is especially obvious when comparing the specific activity of the skeleton catalysts under test. Since the tested catalysts have been taken in an equal amount of 2.0 g each, the nickel content therein has been different accordingly, e.g. in catalyst No.2, 0.96 g; No.5, 0.8 g; No.7, 0.2 g.

As seen from Table 1 catalysts Nos. 2 and 7 enable almost equal extent of glucose conversion to be attained, whereas the ratio of nickel content in said catalysts is 5:1 respectively. Hence, the specific activity of skeleton Ni-Fe catalysts is nearly five times that of a skeleton Ni-Ti catalyst.

EXAMPLE 2

An important characteristic feature of an effective catalyst is the ability to keep its high activity when repeatedly employed in the hydrogenation process. To substantiate this ability the catalysts have been tested repeatedly by resorting to the following technique: 5.0 g of an alloy composed of Ni, Al and Fe at a ratio of 40:50:10 is subjected to leaching at 100° C in 300 ml of a 20-percent aqueous caustic for one hour, whereupon the tested alloy is washed till a neutral reaction and the process of hydrogenation is carried out as described in Example 1, under the following conditions: temperature of 110°; $P_{H_2}=50$ kg/cm², duration of the process, one hour. After one hour of the hydrogenation process the reaction was stopped and the reaction vessel emptied of the process solution and catalyst.

The catalyst having been allowed to settle down, it was separated from the reaction solution and charged along with a new portion of the glucose solution again into the reaction vessel, whereupon the entire process was repeated several times. The test results data are tabulated in Table 2 below.

Table 2

| Composition of catalyst, per cent | Glucose conversion percentage at the same amount of catalyst used in hydrogenation process Number of tests | | | | |
|---|---|---|---|---|---|
| | 1 | 5 | 10 | 15 | 20 |
| Ni:Al=50:50 | 100 | 70 | 34 | 5 | — |
| Ni:Al:Ti=48:50:2 | 100 | 90 | 73 | 51 | 37 |
| Ni:Al:Fe=40:50:10 | 100 | 96 | 82 | 70 | 60 |

Test results have shown unpromoted skeleton nickel to rapidly lose its activity.

This trend is less manifested in the commercial Ni-Ti catalyst. Introduction of Fe into skeleton nickel allows a still more stable catalyst to be obtained. After a 20 fold hydrogenation the capacity of the herein-disclosed skeleton Ni-Fe catalyst is found to remain nearly twice as high as compared to that of the Ni-Ti catalyst.

EXAMPLE 3

A promoted catalyst of a composition of Ni:Al:Fe=40:50:10 taken as an alloy was tested in a column reaction apparatus under stationary conditions. The catalyst activation procedure used in this case differs from that described in Examples 1 and 2, being similar to a conventional procedure adopted in industry for stationary skeleton catalysts. A column was charged with 6 kg of said catalyst, whereupon water was fed thereinto followed by a 20-percent caustic solution. The rate of elimination of Al from the alloy was judged by the amount of $H_2$ being evolved. Alkali treatment of the alloy was ceased after evolution of an amount of $H_2$ equivalent to a 10-percent aluminum content in the alloy. Thereupon, the alkaline solution was removed from the column, and the catalyst was washed with distilled water till a neutral reaction.

Table 3 contains the test results data of a stationary Ni-Fe catalyst, the test being carried out under the following conditions: a temperature of 120° C; $P_{H_2}=65$ kg/cm².

For the sake of comparison given below are the test results data of a commercial skeleton Ni-Ti catalyst tested under similar conditions.

Table 3

| Glucose-to-catalyst charge ratio, kg/kg per hour | Time for 100-percent yield of hexitol, hrs | |
|---|---|---|
| | Ni—Fe | Ni—Ti |
| 0.018 | | 25 |
| 0.012 | | 10 |
| 0.06 | 100 | catalyst inactive |
| 1 | 2 | 3 |
| 0.08 | 24 | '' |
| 0.12 | 28 | '' |
| 0.18 | 8 | '' |
| 0.12 | 380 | '' |

Table 3 contains data obtained from the first (once-through) leaching of the alloys. Gradual increase in the glucose charge rate is explained by the necessity to reveal the maximum (limiting) charge values which are liable to cause the symptoms of catalyst inactivation. As a result, an increase in the glucose conversion degree up to 98 percent has been proven to occur after an 8-hour period of operation on a Ni-Fe catalyst at a charge rate of 0.18 hr⁻¹. After the charge rate on the same catalyst had been diminished below the critical value, i.e., down 0.12 hr⁻¹, the catalyst worked as long as 380 hours more at a 100-percent yield of hexitol. A commercial Ni-Ti catalyst under the same conditions was found to lose its activity even at lower charge rates. On the basis of the investigation carried out it was found that the use of a skeleton Ni-Fe catalyst is instrumental in processing an amount of glucose by a few dozens in excess of that in the case of a Ni-Ti catalyst.

The product of the glucose hydrogenation process, viz., sorbitol when subjected to paper chromatography, is found to possess high purity and not to contain any admixtures.

What is claimed is:

1. A method of producing a polyhydric alcohol comprising hydrogenating a solution of a monose in the presence of a catalyst consisting essentially of Ni and Fe in the ratio from 24:1 to 1:1 at a temperature of from 20° to 120° C. and a hydrogen pressure of 10 to 80 kg/cm², the catalyst being obtained by aqueous caustic leaching of an alloy of nickel, aluminum and iron.

2. The method of claim 1 wherein the ratio of Ni to Fe is 24:1.

3. The method of claim 1 wherein the ratio of Ni to Fe is 9:1,

4. The method of claim 1 wherein the ratio of Ni to Fe is 4:1.

5. The method of claim 1 wherein the ration of Ni to Fe is 1:1.

6. The method of claim 1 wherein the monose is glucose.

7. The method of claim 1 wherein the monose is xylose.

8. The method of claim 2 wherein the monose is glucose.

9. The method of claim 3 wherein the monose is glucose.

10. The method of claim 4 wherein the monose is glucose.

11. The method of claim 5 wherein the monose is glucose.

* * * * *